United States Patent [19]

Prevatt et al.

[11] Patent Number: 5,204,261
[45] Date of Patent: Apr. 20, 1993

[54] **CATALASE-NEGATIVE *PICHIA PASTORIS***

[75] Inventors: William D. Prevatt; George T. Sperl, both of Bartlesville, Okla.

[73] Assignee: Phillips Petroleum Company, Bartlesville, Okla.

[21] Appl. No.: 690,433

[22] Filed: Apr. 24, 1991

[51] Int. Cl.$^5$ ............................................... C12N 1/16
[52] U.S. Cl. .................................... 435/255; 435/190; 435/254
[58] Field of Search ................ 435/255, 190, 938

[56] References Cited

U.S. PATENT DOCUMENTS

| | | | |
|---|---|---|---|
| 4,421,668 | 12/1983 | Cox et al. | 252/174.12 |
| 4,439,525 | 3/1984 | Shay et al. | 435/255 |
| 4,540,668 | 9/1985 | Hopkins | 435/190 |
| 4,619,898 | 10/1986 | Hopkins | 435/190 |
| 4,707,449 | 11/1987 | Shay et al. | 435/255 |

FOREIGN PATENT DOCUMENTS

| | | |
|---|---|---|
| 173378 | 3/1986 | European Pat. Off. . |
| 242007 | 10/1987 | European Pat. Off. . |
| 244920 | 11/1987 | European Pat. Off. . |
| 0374282 | 6/1990 | European Pat. Off. . |

*Primary Examiner*—Douglas W. Robinson
*Assistant Examiner*—Marian C. Knode
*Attorney, Agent, or Firm*—Lucas K. Shay

[57] ABSTRACT

A novel strain of *P. pastoris* and an alcohol oxidase free of catalase activity produced therefrom is provided.

1 Claim, No Drawings

CATALASE-NEGATIVE *PICHIA PASTORIS*

FIELD OF THE INVENTION

This invention relates to catalase-negative *Pichia pastoris* and catalase-free alcohol oxidase produced therefrom.

BACKGROUND OF THE INVENTION

Alcohol oxidase (AO) is an enzyme that catalyzes the oxidation of $C_1$–$C_4$ straight chain alcohols to corresponding aldehydes and thereby produces hydrogen peroxide. The enzyme is produced in methanol-utilizing yeasts such as *P. pastoris, Hanesenula polymorpha*, and *Candida boidinii*, when methanol is present in the growth media. These yeasts assimilate methanol by oxidizing methanol to formaldehyde and hydrogen peroxide. Since the hydrogen peroxide formed is extremely toxic to these yeasts and, it is normally immediately converted to molecular oxygen and water by another enzyme, catalase.

To be useful in washing, bleaching and other aseptic processes, there is a need to produce AO without catalase attached. The AO-catalase enzyme complex produced by methylotrophic yeasts can be isolated from cell-free extracts followed by removal of the catalase so that the catalase-free AO is suitable for use, for example, in a detergent composition to produce hydrogen peroxide upon reaction with a substrate. The process is, however, prohibitively expensive when used to produce catalase-free AO in bulk quantity. Additionally, any residual catalase will still convert hydrogen peroxide to oxygen and water.

Accordingly, it is advantageous to be able to produce AO from yeasts while avoid producing catalase. One such process for producing catalase-free AO has been disclosed. For example, European Patent Application 242,007 discloses the production of catalase-free methanol oxidase in catalase-negative mutants of *Hansenula polymorpha* grown in a nutritive medium suitable for the yeasts in the presence of another source of carbon such as glucose, in which methanol induces the expression of the methanol oxidase gene and is also used as a substrate for the oxidase, while the toxic effects of the hydrogen peroxide produced are circumvented by using a suitable mixing ratio of methanol to other source of carbon. However, such *Hansenula polymorpha* catalase-negative mutants yield only 49% of methanol oxidase with respect to the wild-type strain cultured on methanol.

There is, therefore, a need for a yeast that can produce large quantity of catalase-free AO.

It is therefore an object of the invention to provide a novel *Pichia pastoris* which will produce large quantities of catalase-free AO.

It is also an object of the invention to provide a process to produce the catalase-free AO in high yield by cultivating catalyse-free strain of *P. pastoris* by co-substrate fermentation.

Other aspects, objects, and the several advantages of this invention will be apparent from the following specification and claims.

SUMMARY OF THE INVENTION

In accordance with one aspect of the present invention we have discovered a novel strain of *Pichia pastoris* which will produce catalase-free AO.

In accordance with another aspect of this invention, we have also discovered that an AO free of catalase activity is isolated from the novel strain of *P. pastoris* by a co-substrate fermentation process which comprises growing the novel strain of *P. pastoris* in an aqueous mineral medium containing methanol and a carbon/energy source in a ratio capable of supporting the growth of the yeast and inducing the synthesis of an AO, recovering the yeast cells, and isolating the AO.

DETAILED DESCRIPTION OF THE INVENTION

The novel catalase-negative *P. pastoris* strain is designated as *P. pastoris* NRRL Y-18584.

Samples of our novel *P. pastoris* yeast strain culture have been deposited with the U.S. Department of Agriculture, Agricultural Research Service, Northern Regional Research Laboratory, Peoria, Ill. 61604. The deposit was made in accordance with United States Patent and Trademark Office practice such that all restrictions on availability to the public of samples of the strain will be removed upon granting of a U.S. Patent of which the important strain is the subject.

The novel *P. pastoris* NRRL Y-18584 yeast is derived from wild type *P. pastoris* NRRL Y-11430 by mutations.

The novel yeast *P. pastoris* strain can be conventionally grown in a batch or continuous means.

Aerobic growth on an oxygenated hydrocarbon feedstock is employed in fermentation. Conveniently, the fermentation is conducted in such a manner that the carbon-containing substrate is a limiting factor, thereby providing good conversion of the carbon-containing substrate to yeast cells.

Continuous operation is preferred. During the fermentation, an aqueous mineral medium containing about 5 to about 40% (W/V) (weight/volume) of a suitable carbon/energy source selected from the group consisting of glycerol, glucose, sorbitol, succinate, D,L-alanine, L-proline and mixtures thereof and about 0.5% to about 5% (W/V) of methanol is continuously fed to the fermentor containing the catalase-negative *P. pastoris* strain. The ratio of methanol to the other carbon source is 1:5 to 1:30 (w/w, weight/weight), preferably 1:10 to 1:25 (w/w) and most preferably 1:15 to 1:20 (w/w). The yeast cells are continuously withdrawn for the isolation of catalase-free AO.

The suspended yeast cells are initially separated from the culture medium, for example, by centrifugation or by filtration through filters having a pore size less than the size of the individual cells, and subsequently resuspended in a convenient volume of water or of an appropriate aqueous buffer, for example $KH_2PO_4$/$Na_2HPO_4$ buffer at 0.2M. The pH is not considered critical, however, and the pH of the aqueous suspension does not need to be adjusted prior to homogenization. However, it is considered preferable to adjust the pH broadly in the range of about 6–9, since in this range the enzyme is active and stable.

The cell-containing fluid is homogenized by suitable means known in the art. For example, fermenter effluent containing yeast grown on methanol can be adjusted to a pH of about 7.5 and homogenized at a high cell density concentration such as 100–120 grams biomass (dry weight)/liter using a Dynomill Model KDL using a 0.6 liter vessel in a continuous operation at 5° to 30° C. using belt combination #3 and a flow of 20–30 ml/hr. The homogenate solids are separated from the homogenate to produce a crude solution containing our novel alcohol oxidase as a soluble component. For example, the homogenate solids can be removed by centrifugation to yield a cell-free supernatant. Alternatively the solids can be removed by filtration through filters having a suitable pore size, followed by pH adjustment if desired. If desired, for further purification steps such as recovery of crystalline alcohol oxidase, the pH can be adjusted to have a pH in the range of 5.75 to 6.75 as desired, for example, to pH 6.5.

In the Example provided hereinafter, reference is made to various media. Some media are standard, such as YM, and some are variations of standard media. For convenience, the composition of media referred to herein is shown below in Table I.

Unless otherwise indicated, ingredients below are per liter of water:

TABLE I

I. YM

| | |
|---|---|
| yeast extract | 3 g |
| malt extract | 3 g |
| peptone | 5 g |
| dextrose | 10 g |
| agar | 15 g |

II. FM-21 Media Components

| Component | % Carbon Source Final Concentration | | | | | | |
|---|---|---|---|---|---|---|---|
| | 1 | 10 | 20 | 30 | 40 | 45 | 50 |
| $H_3PO_4$ (85%) (ml) | 0.21 | 2.3 | 5.2 | 9.0 | 14.0 | 17.2 | 21.0 |
| $CaSO_4.2H_2O$ (g) | 0.009 | 0.10 | 0.23 | 0.39 | 0.60 | 0.74 | 0.90 |
| $K_2SO_4$ (g) | 0.143 | 1.6 | 3.6 | 6.1 | 9.5 | 11.7 | 14.3 |
| $MgSO_4.7H_2O$ (g) | 0.117 | 1.3 | 2.9 | 5.0 | 7.8 | 9.6 | 11.7 |
| KOH (g) | 0.039 | 0.43 | 0.98 | 1.7 | 2.6 | 3.2 | 3.9 |
| Biotin (mg) | 0.005 | 0.055 | 0.125 | 0.215 | 0.333 | 0.410 | 0.500 |
| Trace Metals (ml) | 0.098 | 1.1 | 2.4 | 4.2 | 6.5 | 8.0 | 9.8 |

Trace Metals:

| | |
|---|---|
| $FeSO_4.7H_2O$ | 65.0 g/L |
| $CuSO_4.5H_2O$ | 6.0 g/L |
| $ZnSO_4.7H_2O$ | 20.0 g/L |
| $MnSO_4$ | 3.0 g/L |
| $H_2SO_4$ | 5.0 ml/L |
| Antifoam | |
| Carbon Sources | Glucose, Glycerol, Sorbitol, Succinate, D,L-Alanine, L-Proline |

III. IM3 Medium Components

| | |
|---|---|
| Carbon Source | 10.0 g/L |
| $KH_2PO_4$ | 15.0 g/L |
| $K_2HPO_4$ | 1.0 g/L |
| $MgSO_4.7H_2O$ | 0.50 g/L |
| $CaSO_4.2H_2O$ | 0.04 g/L |
| $(NH_4)_2SO_4$ | 3.00 g/L |
| Biotin | 0.05 mg/L |
| Trace Metals | 0.10 ml/L |
| Trace Metals: | |
| $FeSO_4.7H_2O$ | 65.0 g/L |
| $CuSO_4.5H_2O$ | 6.0 g/L |
| $ZnSO_4.7H_2O$ | 20.0 g/L |
| $MnSO_4$ | 3.0 g/L |
| $H_2SO_4$ | 5.0 ml/L |
| Carbon Source | Glucose, Glycerol, Sorbitol, Succinate, D,L-Alanine, L-Proline |
| YPD Medium | 1% Bacto-yeast extract |
| | 2% Bacto-peptone |
| | 2% Dextrose |
| MM (minimal medium) | 0.875 g  $KH_2PO_4$ |
| | 0.125 g  $K_2HPO_4$ |
| | 1.0 g  $(NH_4)_2SO_4$ |
| | 0.5 g  $MgSO_4.7H_2O$ |
| | 0.1 g  NaCl |
| | 0.05 mg  $FeCl_3.6H_2O$ |
| | 0.07 mg  $ZnSO_4.7H_2O$ |

TABLE I-continued

| | | |
|---|---|---|
| | 0.01 mg | $H_3BO_3$ |
| | 0.01 mg | $CuSO_4.5H_2O$ |
| | 0.01 mg | KI |
| | 0.1 g | $CaCl_2.2H_2O$ |
| MM "minus" | MM formulation without $(NH_4)_2SO_4$ | |
| Citrate buffer | 9.79 g | sodium citrate |
| | 3.2 g | citric acid |
| | | dilute to 500 mL with $H_2O$ |
| | | adjust to pH 5.5 with |
| | | 1 N NaOH |
| Nystatin solution | 4.4 mg | nystatin (5680 Units/mg) |
| | 1 mL | dimethylformamide |
| | | dilute to 10 mL with water |

All plate and agar slant media were prepared by adding 15% wt/vol agar to the indicated medium to generate a semi-solid material.

EXAMPLES

The following non-limiting examples are provided to further illustrate the practice of the present invention.

EXAMPLE I

Isolation of Catalase-negative *Pichia pastoris* NRRL Y-18584

A culture of *P. pastoris* NRRL Y-11430 was inoculated into 100 mL of YPD broth and incubated at 30° C. on a shaker for about 12-20 hrs. About 40 mL of the resulting culture were spun down at about 2,000 g for 5 minutes. The cells were then washed twice with 40 ml aliquots of sterile 0.1M citrate buffer (pH 5.5). Washed cells were resuspended in 36 ml of sterile citrate buffer, then treated with 4 mL of NTG solution containing 5 mg of NTG per ml, thus giving a final NTG concentration of 500 μg/ml. Cells in the presence of NTG were allowed to stand for about 30 minutes at room temperature without agitation.

NTG was then removed by washing the cells twice with 40 ml aliquots of sterile deionized water. Sufficient sterile YPD medium was used to resuspend washed cells, which were then transferred to a flask and total volume brought up to 100 ml with additional sterile YPD. These mutagenized cells were then incubated at 30° C. on a shaker for about 48 hours.

After incubation, about 40 ml of the yeast containing solution were spun down at 2,000 g for 5 minutes. The cell pellet was washed twice with 40 ml aliquots of sterile, deionized water, then suspended in 40 ml of sterile MM "minus" media plus 1% glucose carbon source and 5 μg/ml biotin and incubated at 30° C. on a shaker for 12-20 hours.

Five ml of the above culture grown on glucose was used to inoculate 100 ml of sterile "restricted media". Restricted medium consists of the MM formulation plus 1% methanol and 5 mg/l biotin. The inoculum in restricted media was incubated at 30° C. in a shake flask and monitored periodically on a Klett-Summerson photoelectric colorimeter equipped with a 500-570 nm green filter. Incubation was continued until the scale reading (which is proportional to optical density) had increased 20-30% with respect to the original scale reading.

When the scale reading had increased as desired, the solution was treated with 1 ml of Nystatin solution in an amount to give a Nystatin concentration of about 25 units/ml in the solution. The Nystatin-treated solution was incubated at 30° C. for 90 minutes without agitation, at which time 40 ml of the solution was spun down and the cells washed twice with 40 ml aliquots of deionized water. Washed cells were then diluted as appropriate in order to obtain about 100-150 colonies per plate. Colonies were plated on media consisted of MM media 1% glucose and 5 μg biotin. The colonies plated on mutant growth media were replica plated onto media formulation containing 1% methanol and 5 μg/ml biotin. The original and replica plates were incubated at 30° C. for at least 48 hours. Those colonies that grew on the original plate but not on the replica plates were selected for further characterization.

The selected mutants were purified by single colony isolation. A mutant incapable of growing in methanol was found to be defective in catalase activity and was deposited as *P. pastoris* NRRL Y-18584.

EXAMPLE II

This example illustrates that the catalase-negative mutant *P. pastoris* NRRL Y-18584 is incapable of growing with methanol as sole source of carbon and energy and is incapable of producing any catalase activity.

A loopful of yeast from slant culture was inoculated into 100 ml of IM3 aqueous media containing 50 mM methanol and 100 mM other carbon source listed in Table I in a 250 mL Elenmeyer flask. The culture was then grown for 5 days at 30° C. in a shaker shaking at 250 rpm.

The suspended yeast cells can be initially separated from the culture medium, for example, by centrifugation or by filtration through filters having a pore size less than the size of the individual cells, and subsequently resuspended in a convenient volume of water or of an appropriate aqueous buffer, for example $KH_2PO_4/Na_2HPO_4$ buffer at 0.2M. The pH is not considered critical, however, and the pH of the aqueous suspension does not need to be adjusted prior to homogenization. However, it is considered preferable to adjust the pH broadly in the range of about 6-9, since in this range the enzyme is active and stable.

The cell-containing fluid is homogenized by suitable means known in the art. For example, fermenter effluent containing yeast grown on methanol can be adjusted to a pH of about 7.5 and homogenized at a high cell density concentration such as 100-120 grams biomass (dry weight)/liter using a Dynomill ™ Model KDL using a 0.6 liter vessel in a continuous operation at 5° to 30° C. using belt combination #3 and a flow of 20-30 ml/hr. The homogenate solids are separated from the homogenate to produce a crude solution containing my novel alcohol oxidase as a soluble component. For example, the homogenate solids can be removed by centrifugation to yield a cell-free supernatant. Alternatively the solids can be removed by filtration through filters having a suitable pore size, followed by pH adjustment if desired. If desired, for further purification steps such as recovery of crystalline alcohol oxidase, the pH can be adjusted to have a pH in the range of 5.75 to 6.75 as desired, for example, to pH 6.5.

The alcohol oxidase activity for reaction with methanol was determined by the following assay procedure. A dye-buffer mixture was prepared by mixing 0.1 ml of an o-dianisidine solution (1 weight % o-dianisidine in water) with 12 ml of aerated 0.1M sodium phosphate buffer (pH 7.5). The assay mixture was prepared with 2.5 ml of the dye-buffer mixture, 50 μl of methanol, 10 μl of a peroxidase solution (1 mg of horse-radish peroxidase-Sigma, Type II), and 25 μl of the alcohol oxidase solution. The assay mixture was maintained at 25° C. in a 4×1×1 cm cuvette and the increase in absorbance by the dye at 460 nm was recorded for 2 to 4 minutes. The enzyme activity was calculated by $$\text{Activity } (\mu\text{mole/min/ml}) = (\Delta A/\text{min}) \times 11.5$$

wherein 11.5 is a factor based on a standard curve prepared with known aliquots of $H_2O_2$ and $\Delta A$ is the change in absorbance during the experimental interval.

Immediately prior to measurement for catalase activity, cell extract was diluted to give 5-20 units of enzyme activity as defined below in 0.05 M potassium phosphate buffer, pH 7.0. Pipette the following into a 4×1×1 quartz cuvette: 1.9 ml of distilled water and 1.0 ml of 0.059M $H_2O_2$ (in 0.05M potassium phosphate buffer, pH 7.0). Set spectrophotometer to 240 nm and incubate cuvette in spectrophotometer for 5 min. to achieve temperature equilibration and to establish a blan rate (if any). Add 0.1 ml of the diluted cell extract and record decrease in absorbance at 240 nm for 3 min. Calculate $\Delta A_{240}/\text{min}$. from the initial (45 second) linear portion of the curve.

$$\mu\text{moles/ml/min} = \frac{\Delta A_{240}/\text{min} \times DF}{\epsilon \times b}$$

where
$\epsilon = 43.6 \times 10^{-3}$ ml $\mu\text{moles}^{-1}$ cm$^{-1}$
$b = 1$ cm;
1 unit = that amount necessary to oxidize 1 μmole of $H_2O_2$ at pH 7.0 and 22° C. for 1 minute; and
DF is a dilution factor = dilution of the extract in buffer × 20

Therefore, $$\text{units/min/ml} = \frac{\Delta A_{240}/\text{min} \times DF \times 1000}{43.6}$$

After determining protein, catalase activity in units/mg protein can be calculated using the following formula:

$$\text{units/mg} = \frac{\text{units catalase/ml extract}}{\text{mg protein/ml extract}}$$

Protein was determined by measuring absorption of the extract at 280 nm in a 1 cm light path.

$$\text{mg protein/ml} = A_{280} \times 0.667$$

The results are shown in Table II.

TABLE II

Alcohol Oxidase and Catalase Activity of *P. pastoris* NRRL Y-18584 Grown on Mixed Substrates

| carbon source | Growth | AO Specific Activity (Eu/mg protein) | Catalase Specific Activity (Eu/mg protein) |
|---|---|---|---|
| glucose | + | NA | NA |
| D-rhamnose | + | NA | NA |
| D-mannose | + | NA | NA |
| D-fructose | + | NA | NA |
| D.mannitol | + | 1.275 | NA |
| D,L-alanine | + | 0.401 | NA |
| D,L-proline | + | 0.072 | NA |
| succinate | + | 3.900 | NA |
| aceta:e | + | NA | NA |
| ethanol | + | NA | NA |
| methanol | — | did not grow | did not grow |
| glycerol | + | NA | NA |

NA, no activity detected

As shown in Table II, the catalase-negative strain NRRL Y-18584 failed to grow in media containing methanol as sole carbon/energy source. It also shows that no catalase activity was detected in the mutant cells grown on the mixed substrates tested.

EXAMPLE III

This example illustrates that a large quantity of catalase-free AO, with respect to the AO produced in wild-type strain, is produced by the novel yeast mutant *P. pastoris* NRRL Y-18584.

The experiments were carried out the same as in Example II using both wild type and invention yeast strain grown on mixed substrates containing 50 mM MeOH and 100 mM D-sorbitol. The results are shown in Table III.

TABLE III

Growth of *P. pastoris* NRRL Y-18584 and *P. pastoris* NRRLY-11430 in MeOH-Sorbitol

| Strain | Methanol | AO/mg protein | Catalase/mg protein |
|---|---|---|---|
| Y-18584 (Invention) | — | none detected | none detected |
| Y-18584 (Invention) | + | 0.8536 | none detected |
| Y-11430 (Wild Type) | — | none detected | + |
| Y-11430 (Wild Type) | + | 1.26 | +++ |

The results indicate no AO activity was detected in cells grown on methanol-free media. The results also indicate that the mutant yeast produced high AO activity (0.8536 EU/mg protein) while no catalase activity was detected when the cells were grown on mixed substrates. The AO activity presented in the mutant was about 68% of that presented in the parent strain.

EXAMPLE IV

Effects of Inducer on Alcohol Oxidase Production in *P. pastoris* NRRL Y-18584

This example illustrates that alcohol oxidase may be produced continuously from *P. pastoris* NRRL Y-18584 when grown under carbon limiting conditions in the presence of methanol as an inducer.

A loopful of *P. pastoris* NRRL Y-18584 cells from an agar slant or containing YM medium was innoculated into a 250 ml Erlenmeyer flask containing 100 ml of IM3 medium (Table I). The flask was incubated at 30° C. on an orbital shaker with 10 cm strokes at 200 rpm for about 20 hours. The overnight culture was then used as an inoculum for a bench top fermentor.

The bench top fermentor was a custom built (by Phillips Petroleum Company, Bartlesville, Okla.) 4 liter fermentor equipped with monitors and controls for pH, dissolved oxygen, temperature, agitation speed, and air flow. The fermentor was initially loaded with 2 liters of sterile FM-21 medium (Table I). After inoculation with 100 ml of culture, the fermentor was operated aerobically at pH 4.0 and 30° C. for 13 to 16 hours until all the initial carbon source was consumed. Sterile feed containing 100 g/l glycerol and 0–30 g/l methanol or 100 g/l formate was then continuously added at a rate equal to consumption of the glycerol by the growing culture. This was monitored by the dissolved oxygen response. The ungassed liquid volume of the fermentor was maintained at 1.8 to 2.0 liters by continuous withdrawal of the fermentor broth. Air was sterilized by filtration and sparged into the fermentor. Dissolved oxygen was maintained between 50 and 60% of saturation by regulating sparging rate and agitator speed. Gaseous ammonia was used to control pH and as a nitrogen source. Steady state was achieved when there was no change in cell mass at a constant dilution rate for three generations.

Samples of fermentation broth were withdrawn for the measurement of cell concentration, alcohol oxidase activity, and catalase activity as described in Example II. Results are shown in Table IV.

TABLE IV

Alcohol Oxidase and Catalase Activity of *P. pastoris* NRRL Y-18584 Grown Under Carbon Limiting Conditions

| Carbon Source | Inducer | WCDW (g/l) | Alcohol Oxidase Eu/mg Protein | Catalase Eu/m Protein |
|---|---|---|---|---|
| 10% glycerol | none | 59.4 | 0.1192 | NA |
| 10% glycerol | 1% formate | 54.5 | 0.2889 | NA |
| 10% glycerol | 0.5% formaldehyde | 53.4 | 0.1186 | NA |
| 10% glycerol | 1% methanol | 55.9 | 0.6992 | NA |
| 1o% glycerol | 2% methanol | 53.3 | 0.9938 | NA |
| 10% glycerol | 3% methanol | 52.9 | 0.1684 | NA |
| 10% glycerol | none | 58.7 | NA | NA |
| 10% glycerol | 1% n-butanol | | culture death | |

WCDW, whole cell dry weight
NA, no activity detected

As shown in Table IV, the catalase mutant produced a small amount of alcohol oxidase without an inducer due to partial relief of catabolite repression during glycerol limited growth. Formate appeared to act as a poor inducer and, when added to the feed, increased alcohol oxidase specific activity (2×) over background levels; however, formaldehyde showed no ability to induce alcohol oxidase and would be toxic to the culture at higher concentrations. Methanol, at 1–2% concentrations in the feed, caused a 6–9× increase in alcohol oxidase specific activity, and was the best inducer. At these concentrations, no methanol was detected in the fermentor output, indicating that methanol was consumed during growth of the culture. However, with 3% methanol in the feed, alcohol oxidase was reduced to background levels and 0.9% methanol was detected in the fermentor output, indicating that the methanol concentration had exceeded the metabolic capabilities of the culture. Butanol, a potential non-utilizable inducer, was toxic to the culture. Catalase activity was never detected.

Also within the scope of this invention are mutants of *P. pastoris* derived, by genetic manipulation techniques, from this strain which retain strain NRRL Y-18584's abilities to grow on both methanol and other carbon/energy source and to produce catalase-free AO.

The examples have been provided merely to illustrate the practice of the invention and should not be read so as to limit the scope of the invention or the appended claims in any way. Reasonable variations and modifications, not departing from the essence and spirit of the invention, are contemplated to be within the scope of patent protection desired and sought.

That which is claimed is:

1. A biologically pure culture of *Pichia pastoris* strain NRRL Y-18584.

* * * * *